US00PP30778P3

(12) United States Plant Patent
Stemkens

(10) Patent No.: US PP30,778 P3
(45) Date of Patent: Aug. 6, 2019

(54) ***VERBENA* PLANT NAMED 'VEAZ0053'**

(50) Latin Name: *Verbena hybrida*
Varietal Denomination: VEAZ0053

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/999,980

(22) Filed: Sep. 10, 2018

(65) Prior Publication Data

US 2019/0104666 P1 Apr. 4, 2019

(30) Foreign Application Priority Data

Oct. 2, 2017 (QZ) ..... PBR 2017/2458

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
See application file for complete search history.

(56) References Cited

PUBLICATIONS

PLUTO Plant Variety Database Apr. 11, 2019.*

* cited by examiner

*Primary Examiner* — Annette H Para
(74) *Attorney, Agent, or Firm* — Dale Skalla

(57) ABSTRACT

A new *Verbena* plant named 'VEAZ0053' particularly distinguished by medium sized inflorescences, medium sized flowers, that are bicolor, dark rose and pink, dark green, undivided leaves, and an upright plant habit.

1 Drawing Sheet

Latin name of the genus and species of the plant claimed: *Verbena hybrida.*

Varietal denomination: 'VEAZ0053'.

BACKGROUND OF THE NEW PLANT

The present invention comprises a new *Verbena*, botanically known as *Verbena hybrida*, and hereinafter referred to by the variety name 'VEAZ0053'.

'VEAZ0053' is a product of a planned breeding program. The new cultivar has medium sized inflorescences, medium sized flowers, that are bicolor, dark rose and pink, dark green, undivided leaves, and an upright plant habit.

'VEAZ0053' originated from a selfing made in July 2013 in the greenhouse in Enkhuizen, The Netherlands.

The female (and also male) parent was the patent applied plant designated 'VEAZ0050' application Ser. No. 16/350,008, having a flower color that is dark lavender with light lavender bicolor, medium sized leaves, and an upright plant habit.

The resulting seed was sown in February 2014 in a greenhouse in Enkhuizen, The Netherlands. 'VEAZ0053' was selected as one flowering plant within the progeny of the stated cross in May 2014.

The first act of asexual reproduction of 'VEAZ0053' was accomplished when vegetative cuttings were propagated from the initial selection in June 2014 in a greenhouse in Enkhuizen, The Netherlands.

BRIEF SUMMARY OF INVENTION

Horticultural examination of plants grown from cuttings of the plant initiated in the fall of 2014, and continuing thereafter, has demonstrated that the combination of characteristics as herein disclosed for 'VEAZ0053' are firmly fixed and are retained through successive generations of asexual reproduction.

'VEAZ0053' has not been observed under all possible environmental conditions. The phenotype may vary significantly with variations in environment such as temperature, light intensity, and day length.

A Plant Breeder's Right for this cultivar was applied for in the European Union on Oct. 2, 2017, No. 2017/2458. 'VEAZ0053' has not been made publicly available prior to the effective filing date of this application, notwithstanding any disclosure that may have been made less than one year prior to the effective filing date of this application by the inventor or another who obtained 'VEAZ0053' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0053' with colors being as true as possible with an illustration of this type.

Figure 1:
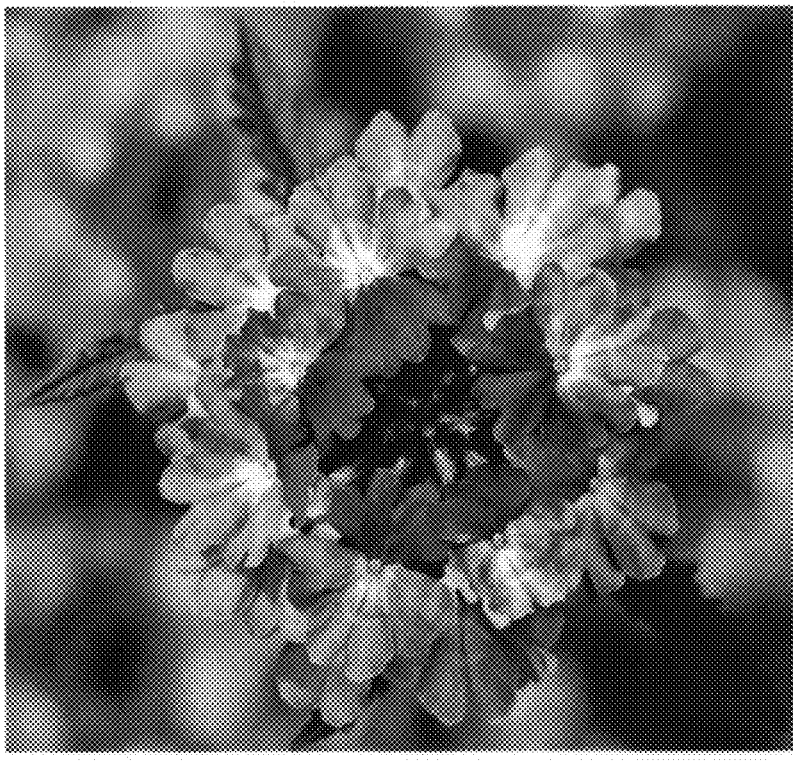
Figure 2:
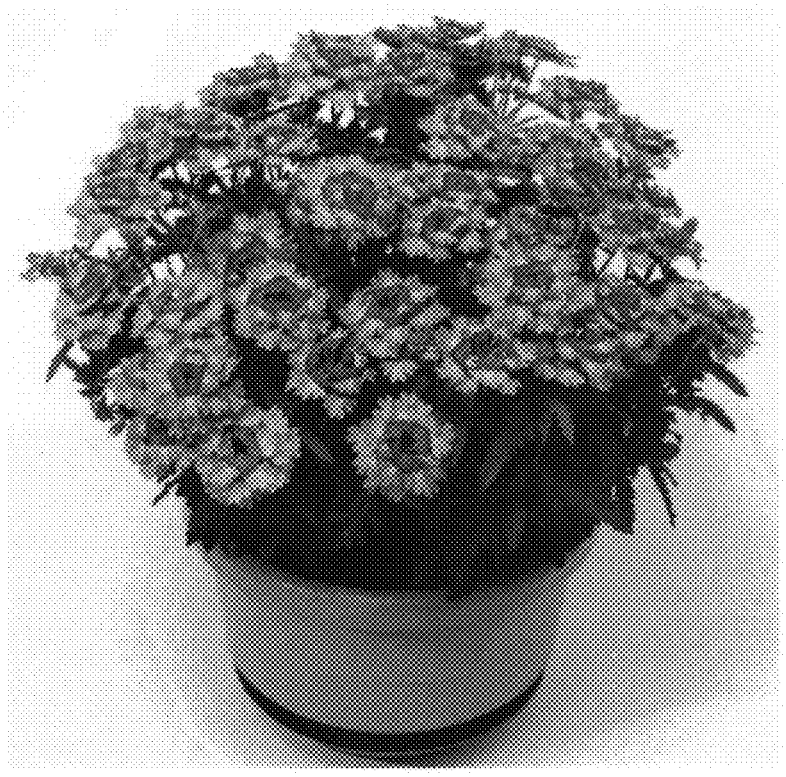

FIG. 1 shows a close view of an inflorescence of the new plant and in FIG. 2 a whole flowering plant. The aforementioned photographs were taken in late May 2018 in Andijk, The Netherlands. The plants were about 10 weeks old and were grown in 12 cm pots.

DETAILED BOTANICAL DESCRIPTION

Color references are made to The Royal Horticultural Society Colour Chart (R.H.S.) 2001.

TABLE 1

DIFFERENCES BETWEEN THE NEW VARIETY 'VEAZ0053' AND A MOST SIMILAR VARIETY

| | 'VEAZ0053' | 'VEAZ0042' (U.S. Pat. No. PP29,517) |
|---|---|---|
| Flower color | Two tones of rose and pink | Red and white |
| Flower size: | Medium | Large |
| Leaf size: | Smaller | Larger |

Plant:

*Form, growth and habit.*—Herbaceous, initially upright, then outwardly spreading; vigorous and free-branching.

*Plant height.*—16 cm.

*Plant height (inflorescence included).*—18.4 cm.

*Plant width.*—24.5 cm.

Roots:

*Number of days to initiate and produce roots.*—11-14 days at about 22 degrees C.

*Type.*—Fine, fibrous, free branching.

*Color.*—RHS N155D but whiter.

Foliage:

*Arrangement.*—Opposite, simple.

*Immature, leaf color, upper surface.*—RHS 137B.

*Immature, leaf color, lower surface.*—RHS 137C.

*Mature, leaf color, upper surface.*—RHS 137A.

*Mature, leaf color, lower surface.*—RHS 137C.

*Length.*—About 3 cm.

*Width.*—2.2-2.4 cm.

*Shape.*—Ovate.

*Base shape.*—Cordate.

*Apex shape.*—Acute.

*Margin.*—Dentate.

*Texture, upper surface.*—Hirsute.

*Texture, lower surface.*—Hirsute.

*Color of veins, upper surface.*—RHS 138B.

*Color of veins, lower surface.*—RHS 137B.

*Pattern of veining.*—Pinnate.

*Petiole color.*—RHS 137B.

*Petiole length.*—1 cm.

*Petiole width.*—0.3 cm.

*Texture.*—Hirsute.

Stem:

*Branching characteristics.*—Makes branches on every node.

*Quantity of main branches per plant.*—About 29.

*Color of stem.*—RHS 137B.

*Stem length.*—12 to 17 cm.

*Stem width.*—0.4 cm.

*Length of internodes.*—2-4 cm.

*Texture.*—Hirsute.

*Color of peduncle.*—RHS 137B.

*Length of peduncle.*—About 2-2.2 cm.

*Peduncle diameter.*—0.2 cm.

*Texture.*—Canescent.

Inflorescence:

*Type.*—Umbel-like, but actually a spike, umbrella-shaped, large.

*Blooming habit.*—Flowers continuously through the summer months.

*Lastingness of individual blooms on the plant.*—About 5 days in the greenhouse.

*Fragrance.*—None.

*Number of inflorescences per plant.*—30 to 38 at various stages.

*Horizontal diameter of inflorescence.*—About 5.5 cm.

*Depth of inflorescence.*—3.1 cm.

*Number of florets per inflorescence (including any buds at the time).*—16-30.

Bud (just when opening/showing color):

*Color.*—RHS N74C.

*Length.*—0.4 cm.

*Width.*—0.4 cm.

*Shape.*—Tubular with a bulbous end.

Floret:

*Form.*—Sessile; salver-shape, composed of 5 partly fused petals with a base of a narrow tube.

*Immature color, 2 upper petals, upper surface.*—RHS 46D.

*Immature color, 2 upper petals, lower surface.*—RHS 75D.

*Mature color, 2 upper petals, upper surface.*—RHS 46C.

*Mature color, 2 upper petals, lower surface.*—RHS 75D.

*Immature color, 3 lower petals, upper surface.*—RHS N66B.

*Immature color, 3 lower petals, lower surface.*—RHS 75D.

*Mature color, 3 lower petals, upper surface.*—RHS N66A.

*Mature color, 3 lower petals, lower surface.*—RHS 75D.

*Floret diameter.*—2.4 to 2.8 cm.

*Floret length (depth).*—2.1-2.4 cm.

*Number of petals.*—Gamopetalous, 5 lobed.

*Petal length.*—1.5 cm.

*Petal width.*—1 cm.

*Shape.*—Obcordate.

*Apex shape.*—Emarginate.

*Margin.*—Entire.

*Petal texture, upper surface.*—Papillose; glabrous.

*Petal texture, lower surface.*—Papillose.

*Corolla tube length.*—1.4 cm.

*Corolla tube width.*—0.2 cm.

*Corolla tube color inside.*—RHS 75B.

*Tube color outside.*—RHS N74C.

*Corolla texture, inside.*—Papillose.

*Corolla texture, outside.*—Glabrous.

*Throat hair color.*—RHS 155B.

Calyx:

*Type.*—Five sepals whose margins are fused to each other along their length, with a transparent membrane of less than 0.1 cm in width and with one smaller sepal attached to the base of the calyx.

*Color of sepals.*—RHS 137C.

*Length of sepals.*—1.1 cm.

*Width of sepals.*—0.25 cm.

*Sepal shape.*—Linear, but fused.

*Apex shape.*—Acute.

*Margins.*—Entire.

*Texture.*—Densely covered with short hair.

Reproductive organs:

*Gynoecium.*—

*Pistil.*—1.

*Pistil length.*—1.3 cm.

*Style color.*—RHS N144C.

*Style length.*—1.5 cm.

*Stigma color.*—RHS 144C.

*Ovary color.*—RHS 144B.

*Ovary length.*—0.24 cm.

*Ovary width.*—0.1 cm.

*Androecium.*—

*Stamens.*—Anthers and filaments fused to upper half of corolla tube; four anthers with two pollen sacs per anther.

*Color of filaments.*—RHS 151B.

*Filament length.*—0.25 cm.

*Anther color.*—RHS 151B.

*Anther length.*—0.15 cm.

*Pollen amount.*—None observed.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0053' substantially as illustrated and described herein.

* * * * *